(12) United States Patent
Kim et al.

(10) Patent No.: US 11,535,646 B2
(45) Date of Patent: Dec. 27, 2022

(54) METHOD FOR PURIFICATION OF IMMUNOGLOBULIN

(71) Applicant: GREEN CROSS CORPORATION, Gyeonggi-do (KR)

(72) Inventors: Soo-kwang Kim, Gyeonggi-do (KR);
Kyung Hyun Boo, Gyeonggi-do (KR);
Kang Yun Seo, Gyeonggi-do (KR);
Sung Min Choi, Gyeonggi-do (KR);
Jeong Hye Yoon, Gyeonggi-do (KR);
Jin Hyun Park, Gyeonggi-do (KR);
Yeon Hui Kim, Gyeonggi-do (KR)

(73) Assignee: GREEN CROSS CORPORATION, Gyeonggi-Do (KR)

( * ) Notice: Subject to any disclaimer, the term of this patent is extended or adjusted under 35 U.S.C. 154(b) by 389 days.

(21) Appl. No.: 16/758,653

(22) PCT Filed: Oct. 26, 2018

(86) PCT No.: PCT/KR2018/012817
§ 371 (c)(1),
(2) Date: Apr. 23, 2020

(87) PCT Pub. No.: WO2019/083318
PCT Pub. Date: May 2, 2019

(65) Prior Publication Data
US 2020/0347093 A1    Nov. 5, 2020

(30) Foreign Application Priority Data
Oct. 27, 2017   (KR) ........................ 10-2017-0141215

(51) Int. Cl.
*C07K 1/18* (2006.01)
*C07K 1/30* (2006.01)
*C07K 1/34* (2006.01)
*C07K 1/36* (2006.01)
*C07K 16/06* (2006.01)

(52) U.S. Cl.
CPC ............ *C07K 1/18* (2013.01); *C07K 1/30* (2013.01); *C07K 1/34* (2013.01); *C07K 1/36* (2013.01); *C07K 16/065* (2013.01)

(58) Field of Classification Search
None
See application file for complete search history.

(56) References Cited

U.S. PATENT DOCUMENTS

| | | | |
|---|---|---|---|
| 4,764,369 A | 8/1988 | Neurath et al. | |
| 6,281,336 B1 * | 8/2001 | Laursen | A61P 43/00 530/421 |
| 10,287,315 B2 * | 5/2019 | Son | C07K 1/30 |

FOREIGN PATENT DOCUMENTS

| | | |
|---|---|---|
| KR | 100501263 B1 | 7/2005 |
| KR | 101657690 B1 | 9/2016 |
| KR | 20160118298 A | 10/2016 |
| KR | 20160118299 A | 10/2016 |
| KR | 20160124107 A | 10/2016 |
| KR | 100501263 B1 | 7/2021 |
| WO | WO2012135415 A1 | 10/2012 |

OTHER PUBLICATIONS

Bouma, B.N., et al., "Human Blood Coagulation Factor XI", "The Journal of Biological Chemistry", 1977, pp. 6432-6437, vol. 252, No. 18.
Cohn, E.J., et al., "Preparation and Properties of Serum and Plasma Proteins. IV. A System for the Separation into Fractions of the Protein and Lipoprotein Components of Biological Tissues and Fluids", "Journal of the American Chemical Society", Mar. 1, 1946, pp. 459-475, vol. 68.
Kistler, P., et al., "Large Scale Production of Human Plasma Fractions", "Vox Sanguinis", Jul. 8, 1962, pp. 414-424, vol. 7.
Kuby, J., Ed., "Antibodies: Structure and Function, Chapter 4, Figure 14.3", "Kuby Immunology, 4th Edition", 2000, p. 91.

* cited by examiner

*Primary Examiner* — Anand U Desai
(74) *Attorney, Agent, or Firm* — Hultquist, PLLC; Steven J. Hultquist (57) ABSTRACT

The present invention relates to an improved method of purifying an immunoglobulin, and more particularly to a method of purifying an immunoglobulin which is capable of sufficiently removing impurities from an immunoglobulin-containing plasma protein sample through a simple process, comprising a single anion-exchange chromatography and a single cation-exchange chromatography.

8 Claims, 4 Drawing Sheets

METHOD FOR PURIFICATION OF IMMUNOGLOBULIN

CROSS-REFERENCE TO RELATED APPLICATIONS

This application is a U.S. national phase under the provisions of 35 U.S.C. § 371 of International Patent Application No. PCT/KR18/12817 filed Oct. 26, 2018, which in turn claims priority of Korean Patent Application No. 10-2017-0141215 filed Oct. 27, 2017. The disclosures of International Patent Application No. PCT/KR18/12817 and Korean Patent Application No. 10-2017-0141215 are hereby incorporated herein by reference in their respective entireties, for all purposes.

TECHNICAL FIELD

The present invention relates to an improved method of purifying an immunoglobulin, and more particularly to a method of purifying an immunoglobulin which is capable of sufficiently removing impurities from an immunoglobulin-containing plasma protein sample through a simple process, comprising a single anion-exchange chromatography and a single cation-exchange chromatography.

BACKGROUND ART

Immunoglobulins are plasma proteins containing antibodies against various viruses and bacteria, and are used as a drug for preventing or treating diseases by administering the same to a subject who naturally lacks antibodies or a patient who needs artificial supplementation of antibodies due to viral diseases or bacterial diseases.

Skin For the use of such immunoglobulins as pharmaceuticals, immunoglobulins for subcutaneous or intramuscular injection have been prepared according to the cold ethanol fractionation method developed by Cohn & Oncley (Cohn E. et al., J. Am. Chem. Soc., 68:459, 1946) and the modified method developed by Kistler and Nitschmann (Kistler P, Nitschmann H S, Vox Sang, 7:414. 1962).

However, immunoglobulins for intramuscular injection have the following problems: 1) the doses of such immunoglobulins are limited, making it impossible to administer the immunoglobulins in large amounts; 2) the immunoglobulins cause pain at the site injected with the immunoglobulins; 3) the immunoglobulins have low content of natural immunoglobulin G (IgG) having antibody activity; 4) the antibody activity of the immunoglobulins is reduced by protease at the injection site; and 5) the time taken to reach peak plasma concentrations is 24 hours or more.

To solve the problems of intramuscular injection, administration of immunoglobulins by intravenous injection has been attempted, but when immunoglobulin preparations are administered intravenously, a variety of immediate side effects, including breathing difficulty and circulatory system shock, appear due to anaphylactic reaction attributable to aggregates having anti-complementary activity. Such symptoms appear mainly in immunoglobulin-deficient patients, and particularly, a side effect of severe hypersensitivity has been observed in patients whom anti-IgA antibodies are detected.

Therefore, as intravenous injection of immunoglobulins is impossible due to the above-described problems, the development of immunoglobulin preparations suitable for intravenous injection has been required, and methods capable of removing the above-described aggregates and/or preventing aggregate formation during preparation processes have been developed. Intravenous injection of immunoglobulins has become possible as a result of treating immunoglobulins with proteases such as pepsin, papain or plasmin, or chemical substances such as β-propiolactone, to change their structure so as to suppress the formation of immunoglobulin aggregates or destroy immunoglobulin aggregates, thereby reducing the anti-complementary activities of the immunoglobulins.

In first-generation intravenous immunoglobulins (IVIGs), a starting material (Cohn fraction II) was treated with pepsin to remove immunoglobulin aggregates. The above process does not include a column chromatography step, and the prepared product is lyophilized so as to be stably maintained over a suitable period of time, and is dissolved immediately before use. However, it was found that IVIG products manufactured by some manufacturers caused viral infections such as viral hepatitis C, and for this reason, one or more steps of inactivating and/or removing a known virus were added to the preparation process. Thereafter, second-generation IVIG products with low anti-complementary activity and higher stability were released in the mid-1980s, and such IVIG products are purified by several chromatography processes.

Such preparations are injected intravenously, and thus overcome the disadvantages of intramuscular immunoglobulins, including the restriction of a dose, pain at the injection site, and reduced antibody activity of immunoglobulins due to the protease, and the time taken to reach peak plasma concentration is also reduced to several hours or less.

However, the intravenous immunoglobulin products described above have little or no natural IgG with antibody activity due to structural changes thereto, and thus have reduced or no complement-binding ability and also have a blood half-life as short as about 4-12 days, suggesting that they exhibit no satisfactory effects on the prevention or treatment of diseases. Furthermore, the first-generation and second-generation IVIG products prepared in the form of lyophilized powder require additional processes for dissolving the same, and have low dissolution rates. For this reason, liquid IVIG products have been developed, and improved processes are required in order to obtain more stable and pure IVIG products.

As a method for purifying plasma-derived immunoglobulins, multiple ion-exchange chromatography (IEX chromatography) is used to remove impurities. In particular, for ion-exchange chromatography, anion-exchange chromatography and cation-exchange chromatography have been applied to remove major impurities. In a purification process using both anion-exchange chromatography and cation-exchange chromatography, there are many cases in which cation-exchange chromatography is used as a capture ($1^{st}$ column) step, and anion-exchange chromatography is used as a polishing ($2^{nd}$ column) step. In this case, the de-salting of a cation-exchange chromatography completion solution is added for subsequent processing, resulting in complicated overall process and reduced yield. In contrast, when anion-exchange chromatography is used as a capture ($1^{st}$ column) step, the process is simplified, but it is required to develop a process suitable for completely removing major impurities.

Against this technical background, the inventors of the present application have made efforts to develop an efficient process suitable for immunoglobulins. As a result, the inventors of the present invention confirmed that it is possible to remove target impurities and increase overall process yield through a method for purifying an immunoglobulin by sequentially applying anion-exchange chromatography and cation-exchange chromatography, and thus completed the present invention.

DISCLOSURE

Technical Problem

Therefore, the present invention has been made in view of the above problems, and it is an object of the present invention to provide a method of purifying an immunoglobulin that can efficiently remove impurities and a thrombotic substance to produce a stable and high-purity immunoglobulin.

Technical Solution

In accordance with the present invention, the above and other objects can be accomplished by the provision of a method of purifying an immunoglobulin, comprising:

(a) subjecting an immunoglobulin-containing plasma sample to anion-exchange chromatography to obtain a fraction that is not attached to an anion-exchange chromatography column; and (b) subjecting the obtained fraction to cation-exchange chromatography, wherein, after the step of (b) above, additional ion-exchange chromatography is not performed.

DESCRIPTION OF DRAWINGS

The above and other objects, features and other advantages of the present invention will be more clearly understood from the following detailed description taken in conjunction with the accompanying drawings, in which.

DETAILED DESCRIPTION

Unless defined otherwise, all technical and scientific terms used herein have the same meanings as those commonly understood by one of ordinary skill in the art to which the invention pertains. Generally, the nomenclature used herein is well known in the art and commonly used.

An embodiment of the present invention relates to a method of purifying an immunoglobulin, including:

(a) subjecting an immunoglobulin-containing plasma sample to anion-exchange chromatography to obtain a fraction that is not attached to an anion-exchange chromatography column; and (b) subjecting the obtained fraction to cation-exchange chromatography, wherein, after the step of (b) above, additional ion-exchange chromatography is not performed.

The immunoglobulin-containing plasma sample is obtained using a method including: (i) dissolving immunoglobulin-containing plasma protein fraction I+II+III or fraction II+III, and then performing a precipitation reaction by adding a precipitant; and (ii) removing the precipitate and obtaining an immunoglobulin-containing supernatant.

As used herein, the expression "immunoglobulin-containing plasma protein" is meant to encompass cryoprecipitate-free plasma obtained by removing various plasma proteins such as Factor IX and antithrombin from human plasma or human placental plasma, various Cohn fractions, and fractions obtained by ammonium sulfate or PEG precipitation. In particular, as the plasma protein fraction, Cohn fraction II, Cohn fraction I+II+III, or Cohn fraction II+III may be used.

According to the present disclosure, fraction I+II+III or fraction II+III obtained from human plasma was used and prepared according to a conventional Cohn plasma fraction method. A subsequent purification process for removing various lipoproteins, fibrinogens, α-globulin, β-globulin, and various coagulation factors included in fraction I+II+III or fraction II+III was performed.

According to the present disclosure, as human plasma, American plasma approved by biotests, including nucleic acid amplification tests on human immunodeficiency virus (HIV), hepatitis C virus (HCV), hepatitis B virus (HBV) and parvovirus B19, and serological tests, and the plasma stored at −20° C. or less was thawed by reaction in a jacketed vessel at 1° C. to 6° C. for 12-72 hours.

While the plasma was thawed under the above-described conditions, a cryoprecipitate including fibrinogen and coagulation factors was produced, and the produced cryoprecipitate was removed by centrifugation, and cryo-poor plasma from which the cryoprecipitate was removed was recovered. Then, precipitation and filtration processes were repeated, thereby finally obtaining fraction I+II+III.

In a filtration process for isolating immunoglobulin-containing plasma, a filter aid was added and mixed with the cryo-poor plasma which was then separated into a supernatant and a precipitate using a filter press, and as the filter aid, Celpure 300 or Celpure 1000 was used.

In the present invention, the dissolution of fraction I+II+III or fraction II+III in process (i) above is performed by adding distilled water to the fraction I+II+III or fraction II+III and the distilled water may be distilled water for injection.

The plasma protein fraction is preferably suspended (dissolved) in water and/or a buffer at a substantially non-denaturing temperature and pH. The term "substantially non-denaturing" means that the condition to which the term refers does not cause irreversible loss of functional activity of the substantial immunoglobulin molecules, e.g., loss of antigen-binding activity and/or loss of biological Fc-function.

The pH of the immunoglobulin-containing suspension is maintained particularly at a pH of 6.0 or less, and more particularly at a pH of 3.9 to 6.0, to ensure optimal solubility of the immunoglobulin. Any buffer known in the art may be used, but particularly, sodium phosphate, sodium acetate, sodium chloride, acetic acid, sodium hydroxide, hydrochloric acid, water (distilled water), or the like may be used, and in the present invention, distilled water or distilled water for injection was used.

The inventors of the present application confirmed that, when using AEX as a $1^{st}$ column and CEX as a $2^{nd}$ column, the number of overall purification steps was reduced, total yield was increased, and acceptance criteria for quality were satisfied. In addition, to sufficiently remove major impurities using AEX as a $1^{st}$ column, conditions suitable for processes (a) and (b) were identified.

The precipitant may be one or more materials selected from polyethylene glycol (PEG) having various molecular weights, caprylic acid, hereinafter used with caprylate, and ammonium sulfate, and a non-denaturing water-soluble protein precipitant known in the art may be used as a means for precipitation. In particular, caprylic acid may be used. Caprylic acid may be effective for removing non-immunoglobulin impurities, and impurities may be removed by precipitating the same through caprylic acid treatment.

In the precipitation reaction according to process (i), the precipitant may be added at a concentration of 5 mM to 26 mM. In addition, a solution obtained by adding a precipitant to the immunoglobulin-containing plasma protein fraction may be adjusted to have a pH ranging from 4.7 to 5.2.

According to the present disclosure, process (ii) above is a process for removing the precipitate and obtaining an immunoglobulin-containing supernatant.

In process (ii) above, the removal of the precipitate may be performed by filtering the immunoglobulin-containing supernatant through a filter film while applying pressure thereto. According to one embodiment of the present invention, the immunoglobulin-containing supernatant was filtered through a filter film.

Thereafter, the filtrate is dialyzed and/or concentrated, and the dialysis and/or concentration may be performed through ultrafiltration and/or diafiltration (UF/DF). In the ultrafiltration and/or diafiltration, changes to constant osmotic pressure, buffer exchange, and concentration may be adjusted to increase the purity of a target material such as immunoglobulin.

In one embodiment, the pH of the filtrate may be adjusted to 4.2 to 4.8 using an acid or base, for example, acetic acid or sodium hydroxide, followed by a first ultrafiltration (UF) process.

Then, diafiltration may be performed using a diafiltration buffer, e.g., sodium acetate, to recover a diafiltration completion solution.

After process (ii) above, anion-exchange chromatography is performed to obtain a fraction that is not attached to the column, thereby removing impurities and obtaining target IgG.

The pI of IgG is between about 6.4 and about 9.0, and in the range of pH 5.5-6.2, the higher the pH, the weaker the positive charge, and the lower the pH, the weaker the ionic interaction between the IgG and the AEX resin, and the IgG yield of a flow-through mode process may be increased.

The pI of IgA is between about 4.5 and about 5.6, and in the range of pH 5.5-6.2, the higher the pH, the weaker the positive charge and the stronger the negative charge, and thus the lower the pH, the weaker the ionic interaction between the IgA and the AEX resin, and the IgA concentration of a flow-through mode process may be increased.

The pI of IgM is between about 4.5 and about 6.5, and in the range of pH 5.5-6.2, the higher the pH, the weaker the positive charge, and the stronger the negative charge, and thus the lower the pH, the weaker the ionic interaction between the IgM and the AEX resin, and the IgM concentration of a flow-through mode process may be increased.

Polymers also show correlations similar to those in IgA and IgM, and may be removed through pH adjustment in the AEX process. In particular, since IgM takes the form of pentamers, most polymers removed in the AEX process may be IgM.

In anion-exchange chromatography, a pH suitable for allowing impurities to be adsorbed onto anion exchange resin and allowing an immunoglobulin to be recovered via a filtrate was identified, and specifically, in the case of a pH of 5.8 or higher, a pH of 5.8-6.2, particularly 6.0-6.2, and more particularly pH 6.05-6.15, impurities such as IgA, IgM, and polymers may be efficiently removed.

The anion-exchange resin used in the anion-exchange chromatography process may be one substituted with diethylaminoethyl (DEAE) or quaternary ammonium groups, but the present invention is not limited thereto. Specifically, the anion-exchange resin may be any one selected from anion-exchange resins having strongly basic quaternary ammonium groups or weakly basic diethylaminoethyl (DEAE) groups.

For example, as a strongly basic anion exchange resin, Q Sepharose Fast Flow, Q Sepharose High Performance, Resource Q, Source 15Q, Source 30Q, Mono Q, Mini Q, Capto Q, Capto Q ImpRes, Q HyperCel, Q Ceramic HyperD F, Nuvia Q, UNOsphere Q, Macro-Prep High Q, Macro-Prep 25 Q, Fractogel EMD TMAE(S), Fractogel EMD TMAE Hicap (M), Fractogel EMD TMAE (M), Eshmono Q, Toyopearl QAE-550C, Toyopearl SuperQ-650C, Toyopearl GigaCap Q-650M, Toyopearl Q-600C AR, Toyopearl SuperQ-650M, Toyopearl SuperQ-6505, TSKgel SuperQ-5PW (30), TSKgel SuperQ-5PW (20), TSKgel SuperQ-5PW, or the like may be used, but the present invention is not limited thereto, and any anion exchange resin known in the art may be used.

The appropriate volume of resin used in the anion-exchange chromatography is determined by the dimensions of the column, i.e., the diameter of the column and the height of the resin, and varies depending on, for example, the amount of the immunoglobulin in the applied solution and the binding capacity of the resin used. Before performing anion-exchange chromatography, the anion-exchange resin is particularly equilibrated with a buffer which allows the resin to bind to counter ions thereof.

In an exemplary embodiment of the present invention, Fractogel EMD TMAE(S) was used as the anion exchange resin, and the UF/DF-completed solution was adjusted to have a pH of 6.05-6.15 and then loaded into Fractogel EMD TAME(S) with a residence time of 15 minutes or longer.

The method of the present invention includes (b) subjecting the obtained fraction to cation-exchange chromatography after process (a). The method of the present invention may further include, between processes (a) and (b), inactivating viruses by adding a surfactant.

The inactivation of the viruses is a process for inactivating viruses such as potential lipid-enveloped viruses in the immunoglobulin-containing solution, and then removing the substance used for the inactivation.

This process inactivates potential lipid-enveloped viruses, such as HIV1 and HIV2, hepatitis type C and non-ABC, HTLV1 and 2, herpes virus family, CMV, and Epstein-Barr virus, thereby improving the safety of final products.

In this process, any solvent and/or detergent may be used without limitation, as long as it has the capability to inactivate viruses, especially lipid-enveloped viruses. The detergent may be selected from the group consisting of non-ionic and ionic detergents, and is preferably substantially non-denaturing. A non-ionic detergent is particularly preferable in terms of easy removal, and the solvent is most preferably tri-n-butyl phosphate (TNBP) or polysorbate 80 (Tween 80), as disclosed in U.S. Pat. No. 4,764,369, but the present invention is not limited thereto.

In one example of the present invention, a virus inactivation process was performed on the AEX process-completed solution using TNBP and polysorbate 80 (Tween 80).

A suitable solvent/detergent mixture may be added such that the concentration of TNBP in the immunoglobulin-containing solution is between 0.2 wt % and 0.6 wt %, and such that the concentration of Tween 80 is between 0.8 wt % and 1.5 wt %.

The virus-inactivation process is performed under conditions that inactivate lipid-enveloped viruses, thereby producing a substantially virus-safe immunoglobulin-containing solution. Under the above conditions, the reaction temperature is particularly between 4° C. and 30° C., and more particularly between 19° C. and 28° C., and the reaction time is particularly between 1 hour and 24 hours, and more particularly between 4 hours and 12 hours.

The cation-exchange chromatography in process (b) may be a process for releasing the adsorbed IgG using an elution buffer after loading the completed solution treated with a solvent/detergent.

The elution buffer in the cation-exchange chromatography may include one or more selected from the group consisting of sodium citrate, sodium acetate, sodium chloride, sodium phosphate, sodium sulfate, potassium chloride, potassium sulfate, potassium phosphate, Tris, 2-(N-morpholino)ethanesulfonic acid (MES), 4-(2-hydroxyethyl)-1-piperazineethanesulfonic acid (HEPES), and 3-[(3-cholamidopropyl)-dimethylammonio]-1-propane sulfonate (CHAPS), but the present invention is not limited thereto. In one embodiment of the present invention, during the cation-exchange chromatography of process (b), immunoglobulins were eluted using a buffer containing sodium chloride.

In cation-exchange chromatography, it is important to select a suitable NaCl concentration condition for allowing the coagulation factor to tightly bind to the cation-exchange chromatography resin and allowing weakly bound IgG to be recovered via counter ions ($Na^+$) in the elution buffer.

When considering IgG yield in regard to the concentration of NaCl in the elution buffer, it was confirmed that the NaCl concentration of the elution buffer is required to be 200 mM or higher. IgG, which has a pI of about 6.4 to about 9.0, is positively charged at pH 5.2, and thus weakly binds to the cation-exchange chromatography resin. Thus, IgG may be separated well from the resin by counter ions ($Na^+$) added during elution, and the higher the concentration of NaCl in the elution buffer, the higher the concentration of the coagulation factor FXI in an eluate.

Accordingly, the IgG yield and impurity removal rate may be determined according to ionic strength conditions based on the salts included in the elution buffer, and it was confirmed that, when elution was performed at a salt concentration of 200 mM to 300 mM, more particularly 200 mM to 250 mM, and most particularly 220 mM to 240 mM, high IgG yield could be achieved and impurities such as coagulation factors could be efficiently removed.

The cation-exchange resin may be selected from the group consisting of Fractogel, carboxymethyl (CM), sulfoethyl (SE), sulfopropyl (SP), phosphate (P), sulfonate (S), PROPAC WCX-10™ (Dionex), Capto S, S-Sepharose FF, Fractogel EMD SO3M, Toyopearl Megacap II SP 550C, Poros 50 HS, Poros XS, and SP-sepharose matrix, but the present invention is not limited thereto.

In an exemplary embodiment of the present invention, as the cation-exchange resin in process (b), Poros XS was used. The completed solution treated with a solvent and/or a detergent was loaded into a column packed with Poros XS with a residence time of 8-10 minutes or longer, and then the adsorbed IgG was released using an elution buffer containing 150 mM to 300 mM NaCl.

In the method of purifying an immunoglobulin according to the present invention, after process (b), additional ion-exchange chromatography was not performed. In the method of purifying an immunoglobulin according to the present invention, major impurities may be completely removed through only two processes of ion-exchange chromatography.

That is, the method of purifying an immunoglobulin according to the present invention may comprise single anion-exchange chromatography and single cation-exchange chromatography, and additional ion-exchange chromatography is not performed.

According to the present invention, in processes (a) and (b), target impurities may be removed through only precipitation, single anion-exchange chromatography, and single cation-exchange chromatography, thereby obtaining an immunoglobulin with a purity of 96% or more, particularly 98% or more.

In addition, the method of purifying an immunoglobulin according to the present invention does not involve a conventional purification method in which cation-exchange chromatography is followed by anion-exchange chromatography, and thus may not further include, which refers free of, a pH adjustment process, a precipitation process, or a solvent or detergent treatment process, which should be included after cation-exchange chromatography.

Figure 4:
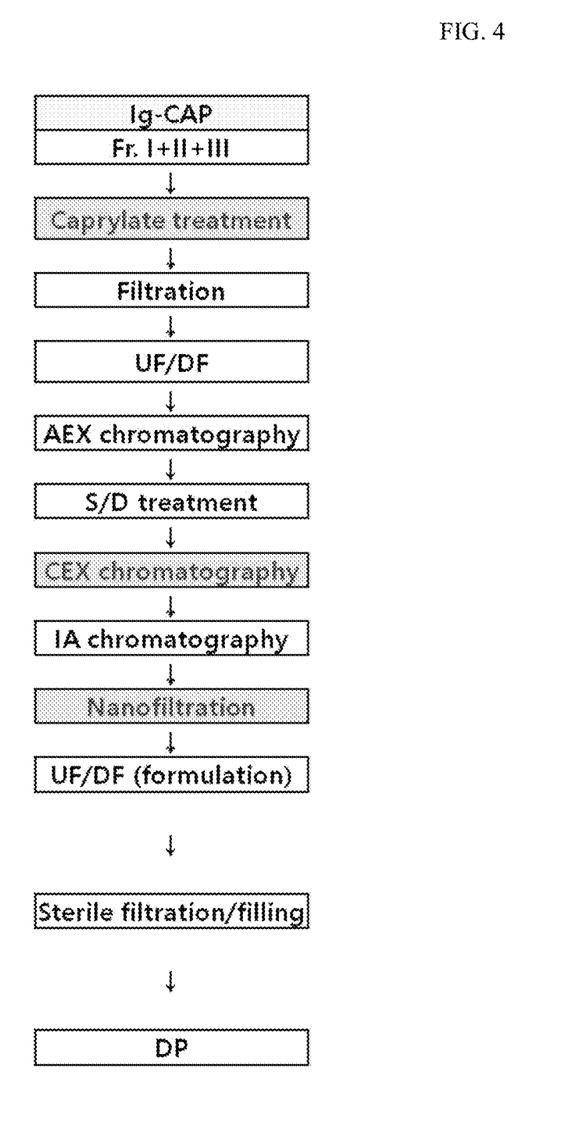
FIG. 4 is a schematic diagram illustrating each process of a purification method according to an embodiment of the present invention.

According to an alternative embodiment, the method of purifying an immunoglobulin according to the present invention may further include, after process (b), immunoaffinity chromatography (FIG. 4). The immunoaffinity chromatography may be any method using an antibody immobilized on an affinity chromatograph. The selective adsorption of immunoglobulins to immobilized antibodies may be induced through specificity and affinity by antibody-antigen interactions. Thereafter, by obtaining target immunoglobulins through elution, a concentration process may be performed simultaneously with purification.

The method may further include, after the immunoaffinity chromatography, a nanofiltration (NF) process.

The nanofiltration may be performed using a commercially available nanofiltration system, and the type of filters used may be Pall DVD pre-filter, DV20, SV4 20N, or Planova 20N, available from Asahi Kasei, but the present invention is not limited thereto.

In some cases, Ultrafiltration/Diafiltration (UF/DF) may be further performed to remove low-molecular-weight ions.

Thereafter, the method may further include adding a stabilizer to prepare immunoglobulins.

In the present invention, an additionally added stabilizer may be one or more selected from sugar alcohol, maltose, sorbitol, mannose, glucose, trehalose, albumin, lysine, glycine, PEG, and Tween 80, and particularly, glycine is used.

EXAMPLES

Hereinafter, the present invention will be described in further detail with reference to the following examples. These examples are provided for illustrative purposes only, and it will be obvious to those skilled in the art that these examples should not be construed as limiting the scope of the present invention.

Example 1: Immunoglobulin Purification 1.1 Purification Column Sequence Process Study 1.1.1. Cation-Exchange Chromatography (CEX) Experimental Conditions after Anion-Exchange Chromatography (AEX)

Fraction I+II+III obtained from human plasma was used and prepared according to a conventional Cohn plasma fractionation method.

Fraction I+II+III Paste Dissolution

Fraction I+II+III paste was stored at a temperature of −30° C. or less and dissolved for 15-21 hours at 2° C. to 8° C. before use.

The dissolved fraction I+II+III paste was dissolved for 30 minutes or longer by adding water for injection, and then adjusted to pH 4.0 using 1M acetic acid or 0.5 N NaOH.

Caprylic Acid Precipitation

A 1M caprylic acid solution was added so that the caprylic acid concentration of the solution was 19 mM to 21 mM.

Filtration

The precipitate solution was filtered using 2-μm and 18-μm filter membranes at a pressure of 2 bar to 3 bar.

To recover the residual IgG from a filter cake produced during the filtration, post washing buffer (20 mM sodium acetate) was added to perform post washing.

$1^{st}$ Ultrafiltration/Diafiltration (UF/DF)

After initial UF, a diafiltration buffer (DF: 20 mM sodium acetate) was used to perform DF, and then the completed solution was recovered.

AEX Chromatography

The $1^{st}$ UF/DF-completed solution was adjusted to have a pH of 6.1 using 1 M Tris, and was then loaded into a column packed with Fractogel EMD TMAE(S).

After loading, the UF/DF-completed solution was recovered using a washing buffer (20 mM sodium acetate pH 6.1).

Solvent/Detergent Treatment (S/D Treatment)

To the AEX process-completed solution, polysorbate 80 1.0 (%, w/v) and tri-n-butyl phosphate (TNBP) 0.3 (%, w/v) were added.

After stirring for 20-30 minutes, a virus inactivation process was performed at 18° C. to 24° C.

CEX Chromatography

The S/D treatment-completed solution was loaded into a column packed with Poros XS.

After loading the completed solution, a washing buffer (20 mM sodium acetate) was allowed to flow a volume that was 6-8 times that of the column, and then the adsorbed IgG was released using an elution buffer (20 mM sodium acetate 230 mM NaCl) to recover the completed solution.

1.1.2. AEX Experimental Conditions after CEX

Fraction I+II+III, obtained from human plasma, was used and prepared according to a conventional Cohn plasma fractionation method.

Fraction I+II+III Paste Dissolution

Fraction I+II+III paste was stored at a temperature of −30° C. or less and dissolved for 15-21 hours at 2° C. to 8° C. before use.

The dissolved fraction I+II+III paste was dissolved for 30 minutes or longer by adding water for injection, and was then adjusted to pH 4.0 using 1M acetic acid or 0.5 N NaOH.

Caprylic acid Precipitation

A 1M caprylic acid solution was added so that the caprylic acid concentration of the solution was 19 mM to 21 mM.

Filtration

The precipitate solution was filtered using 2-μm and 18-μm filter membranes at a pressure of 2 bar to 3 bar.

To recover the residual IgG from a filter cake produced during the filtration, post washing buffer (20 mM sodium acetate) was added to perform post washing.

$1^{st}$ Ultrafiltration/Diafiltration (UF/DF)

After initial UF, a diafiltration buffer (DF: 20 mM sodium acetate) was used to perform DF, and then the completed solution was recovered.

Solvent/Detergent Treatment (S/D Treatment)

To the UF/DF-completed solution, polysorbate 80 1.0 (%, w/v) and tri-n-butyl phosphate (TNBP) 0.3 (%, w/v) were added.

After stirring for 20-30 minutes, a virus inactivation process was performed at 18° C. to 24° C.

CEX Chromatography

The S/D treatment-completed solution was loaded into a column packed with Poros XS.

After loading the completed solution, a washing buffer (20 mM sodium acetate) was allowed to flow at a volume that was 6-8 times that of the column, and then the adsorbed IgG was released using an elution buffer (20 mM sodium acetate 230 mM NaCl) to recover the completed solution.

$2^{nd}$ UF/DF

DF was performed using water for injection, thereby recovering the DF-completed solution.

AEX Chromatography

The $2^{nd}$ UF/DF-completed solution was adjusted to have a pH of 6.1 using 1 M sodium acetate pH 6.1, and was then loaded onto a column packed with Fractogel EMD TMAE (S).

After loading, the UF/DF-completed solution was recovered using a washing buffer (20 mM sodium acetate pH 6.1).

1.2. AEX Chromatography pH Condition Study

Fraction I+II+III obtained from human plasma was used and prepared according to a conventional Cohn plasma fractionation method.

Fraction I+II+III Paste Dissolution

Fraction I+II+III paste was stored at a temperature of −30° C. or less and dissolved for 15-21 hours at 2° C. to 8° C. before use.

The dissolved fraction I+II+III paste was dissolved for 30 minutes or longer by adding water for injection, and was then adjusted to pH 4.0 using 1M acetic acid or 0.5 N NaOH.

Caprylic Acid Precipitation

A 1M caprylic acid solution was added so that the caprylic acid concentration of the solution was 19 mM to 21 mM.

Filtration

The precipitate solution was filtered using 2-μm and 18-μm filter membranes at a pressure of 2 bar to 3 bar.

To recover the residual IgG from the filter cake produced during the filtration, post washing buffer (20 mM sodium acetate) was added to perform post washing.

$1^{st}$ Ultrafiltration/Diafiltration (UF/DF)

After initial UF, a diafiltration buffer (DF: 20 mM sodium acetate) was used to perform DF, and then the completed solution was recovered.

AEX Chromatography

The $1^{st}$ UF/DF-completed solution was adjusted to have a pH of 5.5, 5.6, 5.7, 5.8, 5.9, 6.0, 6.1, and 6.2, respectively using 1 M Tris, and then loaded into a column packed with Fractogel EMD TMAE(S).

After loading, the UF/DF-completed solution was recovered using a washing buffer (20 mM sodium acetate pH 5.5, 5.6, 5.7, 5.8, 5.9, 6.0, 6.1, 6.2).

1.3. Study on NaCl Concentration Conditions for CEX Chromatography Elution Buffer Fraction I+II+III obtained from human plasma was used and prepared according to a conventional Cohn plasma fractionation method.

Fraction I+II+III Paste Dissolution

Fraction I+II+III paste was stored at a temperature of −30° C. or less and dissolved for 15-21 hours at 2° C. to 8° C. before use.

The dissolved fraction I+II+III paste was dissolved for 30 minutes or longer by adding water for injection, and was then adjusted to a pH of 4.0 using 1M acetic acid or 0.5 N NaOH.

Caprylic Acid Precipitation

A 1M caprylic acid solution was added so that the caprylic acid concentration of the solution was 19 mM to 21 mM.

Filtration

The precipitate solution was filtered using 2-μm and 18-μm filter membranes at a pressure of 2 bar to 3 bar.

To recover the residual IgG from a filter cake produced during the filtration, post washing buffer (20 mM sodium acetate) was added to perform post washing.

$1^{st}$ Ultrafiltration/Diafiltration (UF/DF)

After initial UF, a diafiltration buffer (DF: 20 mM sodium acetate) was used to perform DF, and then the completed solution was recovered.

AEX Chromatography

The $1^{st}$ UF/DF-completed solution was adjusted to have a pH of 6.1 using 1 M Tris, and was then loaded into a column packed with Fractogel EMD TMAE(S).

After loading, the UF/DF-completed solution was recovered using a washing buffer (20 mM sodium acetate pH 6.1).

Solvent/Detergent Treatment (S/D Treatment)

To the AEX process-completed solution, polysorbate 80 1.0 (%, w/v) and tri-n-butyl phosphate (TNBP) 0.3 (%, w/v) were added.

After stirring for 20-30 minutes, a virus inactivation process was performed at 18° C. to 24° C.

CEX Chromatography

The S/D treatment-completed solution was loaded into a column packed with Poros XS.

After loading the completed solution, a washing buffer (20 mM sodium acetate) was allowed to flow at a volume that was 6-8 times that of the column, and then the adsorbed IgG was released using an elution buffer (150 mM, 200 mM, 250 mM, or 300 mM NaCl) to recover the completed solution.

Example 2: Results 1.1. Study for Process of Sequential Chromatography

In the case of third-party processes for purifying plasma-derived immunoglobulins, many types of ion-exchange chromatography (IEX) are used to remove impurities. In the case of a process using both AEX and CEX, CEX is often used as a capture ($1^{st}$ column) step and AEX is used as a polishing ($2^{nd}$ column) step, and in this case, for the subsequent process, de-salting of the CEX process-completed solution is added, which complicates the overall process and reduces yield.

In contrast, in the case where AEX is used as a capture ($1^{st}$ column), the process is simplified, but it is required to develop a process suitable for completely removing major impurities.

Figure 1:
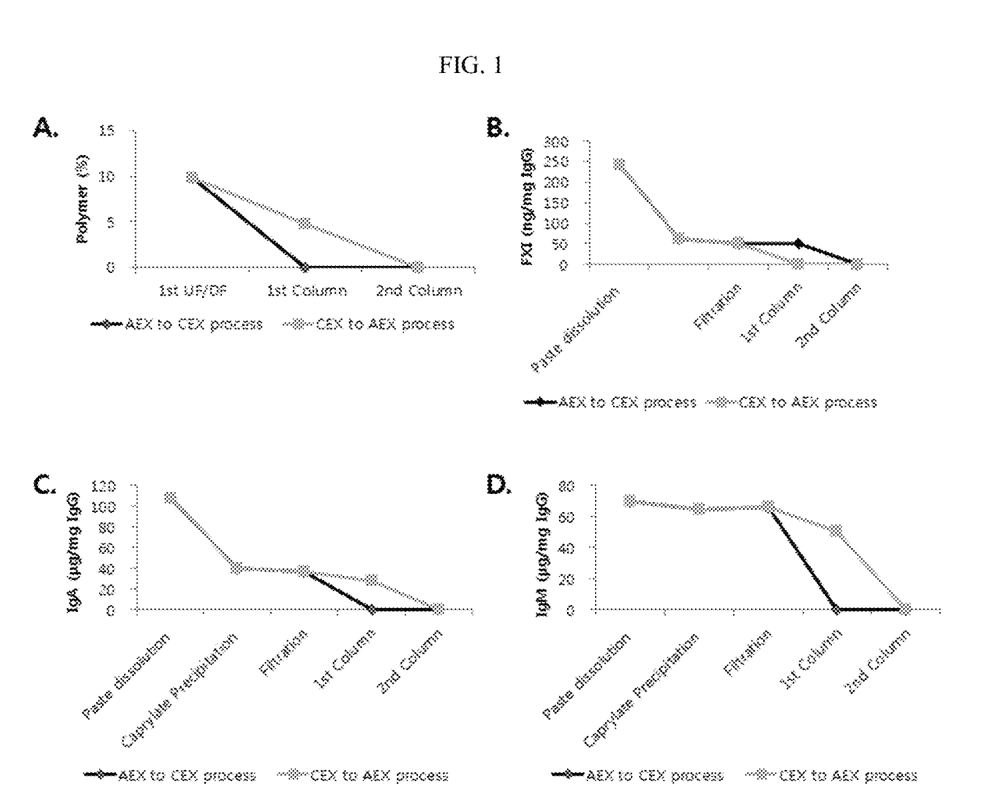
FIG. 1 illustrates impurity removal patterns when the order of AEX chromatography and CEX chromatography was changed in a purification process using the two types of ion-exchange chromatography, wherein, in FIG. 1, A illustrates the amount of polymer, B illustrates the amount of the coagulation factor XI, C illustrates IgA content, and D illustrates IgM content.

As a result of conducting a comparison, in the case where AEX was used as the $1^{st}$ column and CEX was used as the $2^{nd}$ column, the number of overall purification processes was reduced and total yield was increased, and it was confirmed that the case satisfied acceptance criteria for quality (see Tables 1 and 2 and FIG. 1).

TABLE 1

Yield and Impurity Removal Results for Each Process When Using AEX as $1^{st}$ column and CEX as $2^{nd}$ column

| Process (AEX to CEX) | Total yield g/L USP | IgA μg/mg IgG | IgM μg/mg IgG | Human Coagulation Factor XI (FXI) ng/mg IgG | polymer % |
|---|---|---|---|---|---|
| I + II + III paste dissolution | 6.89 | 108.04 | 69.61 | 242.19 | N/A |
| Caprylate precipitation | 5.86 | 40.83 | 64.75 | 63.50 | |
| Filtration | 5.12 | 37.50 | 66.32 | 50.05 | |
| $1^{st}$ UF/DF | 5.17 | 39.85 | 65.12 | N/A | 9.89 |
| AEX Chromatography | 4.86 | 0.33 | 0.00 | | 0.00 |
| CEX Chromatography | 4.37 | 0.35 | 0.00 | 0.01 | 0.00 |
| Acceptance criteria | | ≤0.5 | ≤0.4 | ≤0.01 | ≤3 |

TABLE 2

Yield and Impurity Removal Results for Each Process When Using CEX as $1^{st}$ column and AEX as $2^{nd}$ column

| Process (CEX to AEX) | Total yield g/L USP | IgA μg/mg IgG | IgM μg/mg IgG | FXI ng/mg IgG | polymer % |
|---|---|---|---|---|---|
| I + II + III paste dissolution | 6.89 | 108.04 | 69.61 | 242.19 | N/A |
| Caprylate precipitation | 5.86 | 40.83 | 64.75 | 63.50 | |
| Filtration | 5.12 | 37.50 | 66.32 | 50.05 | |
| $1^{st}$ UF/DF | 5.17 | 39.85 | 65.12 | N/A | 9.89 |
| CEX chromatography | 4.74 | 28.07 | 50.35 | 0.02 | 4.75 |
| $2^{nd}$ UF/DF | 4.68 | N/A | N/A | N/A | 4.68 |
| AEX chromatography | 4.03 | 0.05 | 0.00 | 0.02 | 0.00 |
| Acceptance criteria | | ≤0.5 | ≤0.4 | ≤0.01 | ≤3 |

In particular, AEX chromatography should be performed before CEX chromatography, and it is required to select suitable process conditions for removing major impurities in AEX chromatography. In addition, in the case where additional ion-exchange chromatography is not subsequently performed, it is required to develop suitable process conditions for completely removing major impurities through only the preceding precipitation process and two processes of ion-exchange chromatography.

1.2. Study on pH conditions for AEX Chromatography

The anion-exchange chromatography study results for each pH are shown in Table 3.

TABLE 3

IgG Yield and Impurity Content according to pH in AEX Chromatography Process

| pH | IgG Yield (%) | IgA (μg/mg IgG) | IgM (μg/mg IgG) | polymer (%) |
|---|---|---|---|---|
| 5.5 | 94.71 | 3.63 | 8.79 | 2.69 |
| 5.6 | 100.00 | 2.13 | 2.91 | 1.77 |
| 5.7 | 95.86 | 1.50 | 1.61 | 0.25 |
| 5.8 | 95.62 | 0.68 | <0.02 | 0.00 |

TABLE 3-continued

IgG Yield and Impurity Content according to pH in AEX Chromatography Process

| pH | IgG Yield (%) | IgA (μg/mg IgG) | IgM (μg/mg IgG) | polymer (%) |
|---|---|---|---|---|
| 5.9 | 91.08 | 0.60 | 0.12 | 0.00 |
| 6.0 | 90.45 | 0.34 | <0.02 | 0.00 |
| 6.1 | 88.92 | 0.10 | 0.00 | 0.00 |
| 6.2 | 87.88 | 0.22 | <0.01 | 0.00 |

Figure 2:
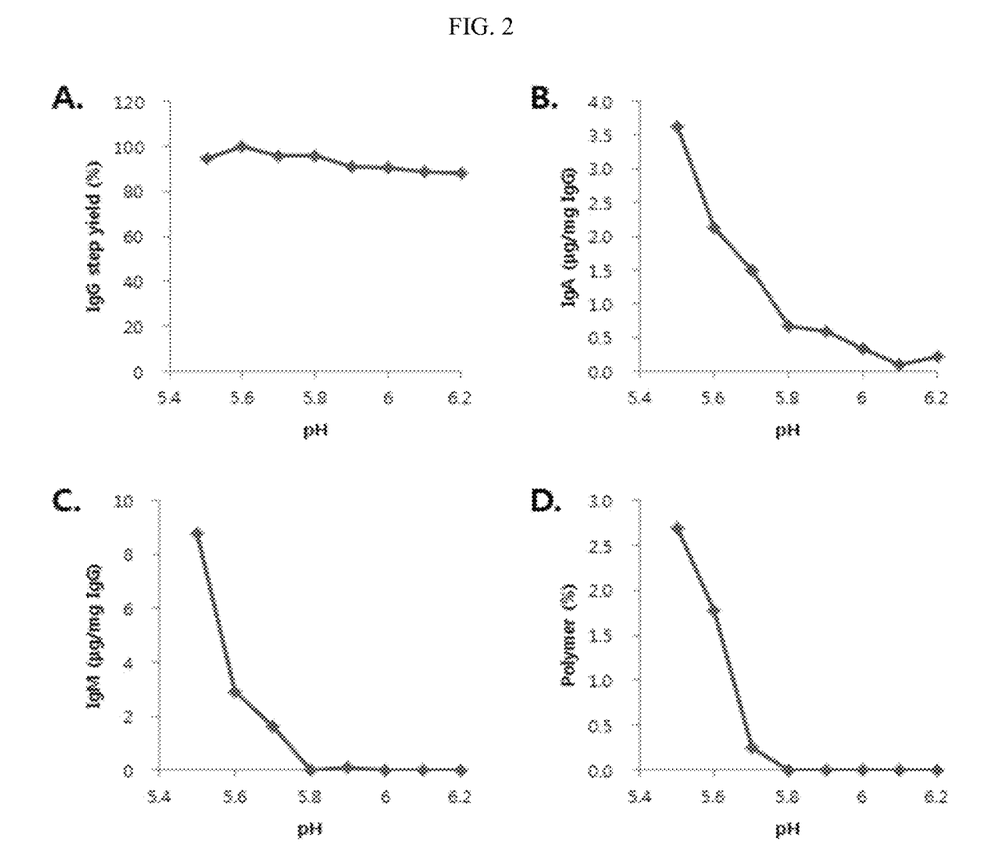
FIG. 2 illustrates IgG yield and the content of impurities according to a pH condition in AEX chromatography, wherein, in FIG. 2, A illustrates IgG yield, B illustrates IgA content, C illustrates IgM content, and D illustrates polymer content.

The pI of IgG has been known to be about 6.4-9.0 (The Human IgG Subclasses. Calbiochem Corporation. 1990), and in the range of pH 5.5-6.2, the higher the pH, the weaker the positive charge. Thus, the lower the pH, the weaker the ionic interaction between IgG and AEX resin and the higher the IgG yield of a flow-through mode process, and the results thereof were obtained as shown in Table 3 and FIG. 2 in graph A therein.

The pI of IgA has been known to be about 4.5-5.6 (Kidney Int 1985; Oct.; 28(4):666-671), and in the range of pH 5.5-6.2, the higher the pH, the weaker the positive charge and the stronger the negative charge. Thus, the lower the pH, the weaker the ionic interaction between the IgA and the AEX resin and the higher the IgA concentration of a flow-through mode process, and a suitable IgA removal rate particularly at a pH of 5.8 or higher was confirmed as shown in Table 3 and FIG. 2 in graph B therein.

The pI of IgM has been known to be about 4.5-6.5 (Electrophoresis, Volume 6, Issue 3, 1985, p 124-128), and in the range of pH 5.5-6.2, the higher the pH, the weaker the positive charge and the stronger the negative charge. Thus, the lower the pH, the weaker the ionic interaction between the IgM and the AEX resin and the higher the IgM concentration of a flow-through mode process, and a suitable IgM removal rate particularly at a pH of 5.8 or higher was confirmed as shown in Table 3 and FIG. 2 in graph C therein.

The correlation between pH and polymers can be confirmed in a form similar to IgA and IgM. In particular, it has been reported that IgM takes the form of pentamers (Kuby Immunology, 4th edition, W.H. Freeman and Company. FIG. 14.3, page 91), and it was determined that most polymers removed during the AEX process were IgM. A suitable polymer removal rate particularly at a pH of 5.8 or higher was confirmed as shown in Table 3 and FIG. 2 in graph D therein.

In anion-exchange chromatography, it is important to select a suitable pH condition for allowing impurities to be adsorbed onto an anion exchange resin and allowing an immunoglobulin to be recovered via a filtrate. In the present invention, to efficiently remove impurities in the anion-exchange chromatography, pH was selected to be particularly 5.8 or higher, more particularly 6.0-6.2, and most particularly 6.05-6.15.

1.3. Study on NaCl Concentration Conditions for CEX Chromatography Elution Buffer CEX chromatography study results according to the ionic strength of an elution buffer are shown in Table 4.

TABLE 4

IgG Yield and Impurity Content according to NaCl Concentration of Elution Buffer in CEX Chromatography.

| Elution buffer NaCl concentration (mM) | IgG step yield (%) | polymer (%) | pg FXI/mg IgG | mU FXIa/mg IgG |
|---|---|---|---|---|
| 150 | 72.7 | 0.00 | N/A | N/A |
| 200 | 89.3 | 0.01 | 58.311541 | <0.0009 |
| 250 | 87.8 | 0.04 | 72.296296 | 0.012 |
| 300 | 87.3 | 0.07 | 92.271084 | 0.016 |

The IgG yield was 72.68% when the NaCl concentration of the elution buffer was 150 mM, and it was confirmed that, when considering the IgG yield, the NaCl concentration of the elution buffer was required to be 200 mM or more. In particular, the pI of IgG has been known to be about 6.4-9.0 (The Human IgG Subclasses. Calbiochem Corporation. 1990), and IgG is positively charged at a pH of 5.2, and thus weakly binds to the CEX resin. Thus, IgG may be separated well from the resin by counter ions ($Na^+$), which are added during elution, and it was determined that the higher the NaCl concentration of the elution buffer, the higher the FXI (human coagulation factor XI) of an eluate.

Figure 3:
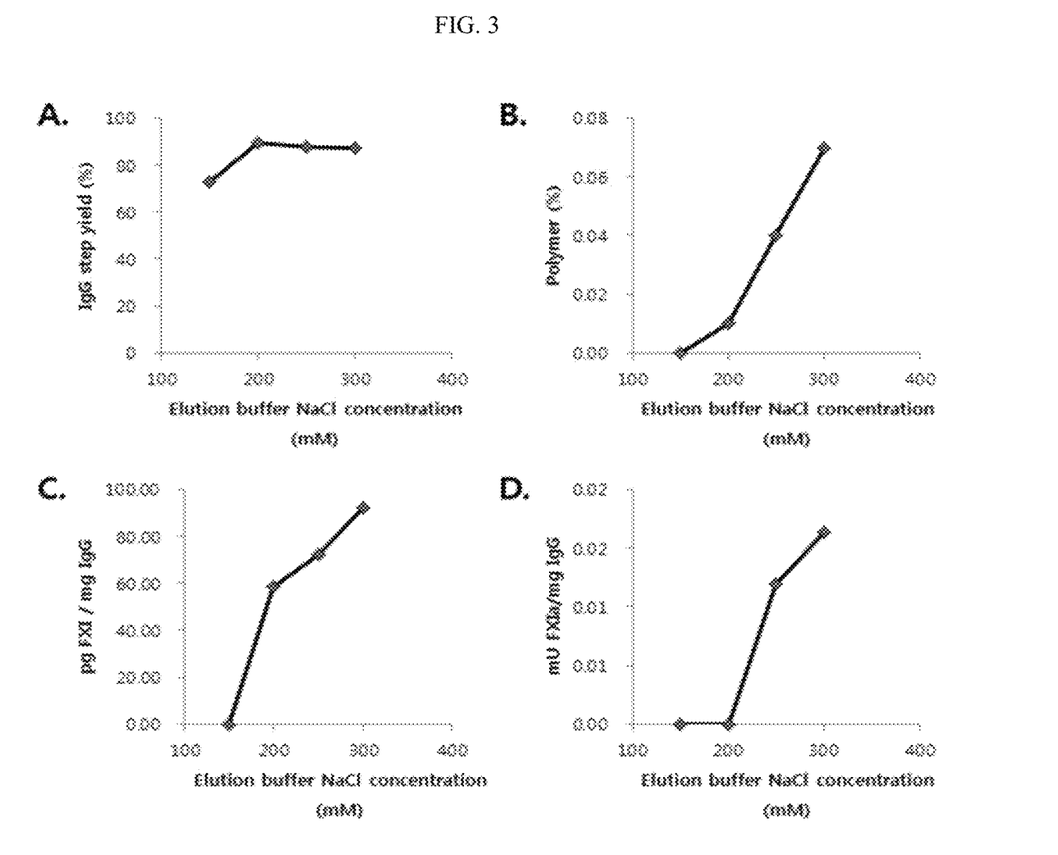
FIG. 3 illustrates IgG yield and the content of impurities according to the concentration of NaCl in an elution buffer in CEX chromatography, wherein, in FIG. 3, A illustrates IgG yield, B illustrates polymer content, C illustrates the content of coagulation factor XI, and D illustrates the content of coagulation factor XIa.

The FXI yield was reduced as the NaCl concentration of the elution buffer was decreased, and it was confirmed that, as compared to a NaCl concentration of 300 mM, the FXI yield was low, i.e., about 40%, at a NaCl concentration of 200 mM. FXIa also exhibited the same pattern as that of the FXI results, and it was confirmed that FXIa was not detected even in a concentrated sample when the NaCl concentration of the elution buffer was 200 mM. In particular, the pI of FXI has been known to be about 9.1 (THE JOURNAL OF Biological chemistry. Vol. 252, No. 18, Issue of Sep. 25, 1977, p 6432-6437), and FXI is positively charged at a pH of 5.2, and thus tightly binds to Poros XS, which is a strong CEX resin. Thus, FXI can be separated well from the resin by counter ions ($Na^x$), which are added during elution, and it was determined that the higher the NaCl concentration of the elution buffer, the higher the FXI concentration of an eluate (see Table 4 and FIG. 3).

In CEX chromatography, it is important to select suitable NaCl concentration conditions for allowing a coagulation factor to tightly bind to the CEX resin and allowing weakly bound IgG to be recovered via counter ions ($Na^+$) in the elution buffer. In the present invention, to efficiently remove impurities in the CEX chromatography, the concentration of NaCl in the elution buffer was selected to be particularly between 200 mM and 300 mM, more particularly between 200 mM and 250 mM, and most particularly between 220 mM and 240 mM.

INDUSTRIAL APPLICABILITY

According to a purification method of the present invention, by simplifying the process, purification of immunoglobulins is possible, total process yield can be increased, the efficiency of removing impurities and a thrombotic substance can be enhanced, and low polymer content can be maintained, and thus immunoglobulins that are stable and satisfy acceptance criteria for quality can be produced.

While specific embodiments of the present invention have been described in detail, it will be obvious to those of ordinary skill in the art that these embodiments are provided for illustrative purposes only and are not intended to limit the scope of the present invention. Thus, the substantial scope of the present invention should be defined by the appended claims and equivalents thereof.

The invention claimed is:

1. A method of purifying an immunoglobulin, the method comprising:
   (a) subjecting an immunoglobulin-containing plasma sample to anion-exchange chromatography to obtain a fraction that is not attached to an anion-exchange chromatography column; and
   (b) subjecting the obtained fraction to cation-exchange chromatography,
   wherein the cation-exchange chromatography of process (b) above comprises eluting the immunoglobulin at a salt concentration of 200 mM to 300 mM, and
   wherein, after process (b) above, additional ion-exchange chromatography is not performed.

2. The method according to claim 1, wherein the immunoglobulin-containing plasma sample is obtained using a method comprising:
   (i) dissolving immunoglobulin-containing plasma protein fraction I+II+III or fraction II+III, and then performing a precipitation reaction by adding a precipitant; and
   (ii) removing the precipitate and obtaining an immunoglobulin-containing supernatant.

3. The method according to claim 2, wherein the precipitant of process (i) above is caprylic acid.

4. The method according to claim 1, wherein the anion-exchange chromatography of process (a) above is performed at a pH ranging from 5.8 to 6.2.

5. The method according to claim 1, wherein the cation-exchange chromatography of process (b) above comprises eluting the immunoglobulin using a sodium chloride-containing buffer.

6. The method according to claim 1, further comprising, between processes (a) and (b) above, inactivating virus by adding a surfactant.

7. The method according to claim 1, wherein an immunoglobulin having a purity of 96% or more is obtained by the method.

8. The method according to claim 1, wherein the method does not further comprise, after process (b) above, a pH adjustment process, a precipitation process, or a solvent or detergent treatment process.

* * * * *

UNITED STATES PATENT AND TRADEMARK OFFICE
CERTIFICATE OF CORRECTION

| | |
|---|---|
| PATENT NO. | : 11,535,646 B2 |
| APPLICATION NO. | : 16/758653 |
| DATED | : December 27, 2022 |
| INVENTOR(S) | : Soo-kwang Kim et al. |

It is certified that error appears in the above-identified patent and that said Letters Patent is hereby corrected as shown below:

In the Specification

Column 6, Line 32, "Toyopearl SuperQ-6505" should be -- Toyopearl SuperQ-650S --.

Signed and Sealed this
Twenty-first Day of February, 2023

Katherine Kelly Vidal
*Director of the United States Patent and Trademark Office*